United States Patent [19]
Kissel et al.

[11] Patent Number: 5,705,357
[45] Date of Patent: Jan. 6, 1998

[54] CHEMILUMINESCENT REAGENT AND ASSAY USING A SUBSTITUTED ACETANILIDE FOR LIGHT GENERATION

[75] Inventors: Thomas Robert Kissel; Alan E. Friedman, both of Rochester; Sarah A. Fingar, Ontario, all of N.Y.

[73] Assignee: Johnson & Johnson Clinical Diagnostics, Inc., Rochester, N.Y.

[21] Appl. No.: 297,475

[22] Filed: Aug. 29, 1994

[51] Int. Cl.$^6$ ..................................................... C12Q 1/28
[52] U.S. Cl. .......................... 435/28; 436/172; 435/7.1
[58] Field of Search ............................ 435/6, 7.1, 7.2, 435/7.21, 7.22, 7.23, 7.24, 7.25, 28; 436/172, 543, 826

[56] References Cited

U.S. PATENT DOCUMENTS 5,279,940 1/1994 Kissel ............................................ 435/6

FOREIGN PATENT DOCUMENTS

| | | | |
|---|---|---|---|
| 252747 | 2/1988 | European Pat. Off. | |
| 455471 | 11/1991 | European Pat. Off. | G01N 33/52 |
| 0 603 954 A3 | 12/1993 | European Pat. Off. | |
| 603953 | 6/1994 | European Pat. Off. | C12Q 1/28 |
| 603954 | 6/1994 | European Pat. Off. | G01N 33/54 |

OTHER PUBLICATIONS

DeToledo et al, *Anal. Biochem.*, 105, 36–38, 1980.
Slawinska et al, *J. Biolum. Chemilum.*, 4, 226–230, 1989.
Segawa et al, *Anal. Sciences*, 6, 763–764, 1990.
Slawinska et al, *J. Luminescence*, 40 & 41, 262–266, 1988.
Koukli et al, *Analyst*, 114, 711–714, 1989.
K. Schmitt, et al., *Photochem. Photobiol.*, "The Peroxidase–Promoted Metabolic Activation of Acetaminophen Produces Electronically Excited Species", vol. 51, No. 6, pp. 719–723, 1990.

*Primary Examiner*—Scott W. Houtteman
*Attorney, Agent, or Firm*—Alan J. Morrison

[57] ABSTRACT

A simplified composition for generating a chemiluminescent signal in the presence of a peroxidase includes a substituted acetanilide as the sole light-producing substrate for the peroxidase. Assays for various analytes can be carried out with this composition at near neutral pH, exhibit low background and are highly sensitive.

17 Claims, 2 Drawing Sheets

CHEMILUMINESCENT REAGENT AND ASSAY USING A SUBSTITUTED ACETANILIDE FOR LIGHT GENERATION

FIELD OF THE INVENTION

This invention relates to a chemiluminescent composition, test kit and method for detection of various analyses using a substituted acetanilide as the sole light generating reagent.

BACKGROUND OF THE INVENTION

It is well known to perform a quantitative or qualitative analysis of an aqueous liquid by contacting that liquid with a combination of reagents capable of yielding a detectable product in proportion to the concentration of the analyte in the liquid. One type of useful assay utilizes enzymatic reactions wherein the analyte, upon contact with the appropriate reagents, reacts with oxygen in the presence of a suitable enzyme to produce hydrogen peroxide in proportion to concentration of the analyte. A detectable product is then produced by the reaction of hydrogen peroxide in proportion to the concentration of the analyte in the test liquid. Peroxidase is generally used in such assays.

In other assays, a peroxidase is reacted in the presence of hydrogen peroxide which has been added to the system to measure the amount of a particular analyte. Analytes such as glucose, triglycerides, uric acid, cholesterol and creatine kinase can be so detected as well as specific binding ligands in specific binding assays wherein the peroxidase is used as a detectable label. Such determinations can be carried out in solution, dry analytical assays or diagnostic test devices. The signals produced in such assays can be a colorimetric, chemiluminescent or fluorescent signal using well known signal generating reagents.

There are several major types of luminescent or luminometric assays which produce an emission of light as a result of the presence of the analyte of interest. These assays are also known as chemiluminescent assays and are described, for example, in U.S. Pat. No. 4,729,950 (Kricka et al) and publications noted therein. Various aromatic amines and phenols, such as p-iodophenol, are considered useful for enhancing the production of light in such assays (see also U.S. Pat. No. 4,598,044 of Kricka et al). One preferred enhancer of colorimetric assays has been 4'-hydroxyacetanilide, which is described in U.S. Pat. No. 4,828,983 (McClune).

Although the enhanced chemiluminescent systems produce adequate light signal for immunoassays, the reagent formulation has certain disadvantages. The optimum pH for light emission using luminol is 8.5. However, the optimum pH for horseradish peroxidase activity is lower (6 to 7). Because of high non-enzymatic oxidation of luminol, background is high and sensitivity is reduced at low enzyme concentrations. Moreover, at the higher pH, the reagent formulation has reduced shelf life (oxidant instability and oxidation of luminol). The need to critically control the activity of several reagents in the formulation presents considerable manufacturing and storage problems.

An improvement in sensitivity was achieved by using cationic micelles with 4'-hydroxyacetanilide as an enhancer, as described in U.S. Pat. No. 5,279,940 (Kissel). However, most of the problems noted above remain even after this advance in the art.

The literature describes a number of peroxidase-based reagent systems which produce light emission without the purposeful addition of a known lumiphore such as luminol, lucigenin, acridinium esters or dioxetanes. It is known, for example, that pyrogallol (1,2,3-trihydroxybenzene) is a substrate for light generation at pH 7. However, the reported sensitivity is quite poor (0.1 nmolar detection limit), and the substrate is considerably unstable from autooxidation. Various enhancers, such as o-phenylenediamine, are known to improve sensitivity, but their use requires management of a more complex and unstable reagent formulation, just as in the case with luminol.

There have been attempts to use conventional fluorescent or phosphorescent dyes as chemiluminescent signal generating substrates for peroxidase. For example, eosin Y has been used with peroxide at pH 6.5 to monitor peroxidase levels down to pmolar concentrations. However, this can only be done by adding the peroxide to the mixture of dye and peroxidase, and when this is done, the background is too high and sensitivity is quite low.

Horseradish peroxidase catalyzed oxidation of ketones and aldehydes such as acetone and propanal can generate light emission with certain fluorescent dyes. However, low turnover number and substrate instability make such systems impractical for commercialization.

It has been observed that light can be generated when the peroxidase is used as an oxidase, such as with NADH, dihydroxyfumarate or luciferin as the substrates. These systems also have their problems, notably poor sensitivity, the need for oxygen in the system (precluding their use in dry analytical elements), and complicated reaction mechanisms.

Koukli et al (*Analyst*, 114, 711, 1989) describes the determination of acetaminophen (4-hydroxyacetanilide) based on the chemiluminescence produced by its reaction with cerium(IV) in acidic solution.

Schmitt et al (*Photochem.Photobiol.*, 31, 719, 1990) demonstrated that 4'-hydroxyacetanilide produces light with peroxidase catalysis in the presence of a cationic micelle. However, only high levels (greater than 10 nmolar) of the peroxidase as the analyte were detectable, and maximum light emission was observed only at pH 8.8. There is no indication that the sensitivity could be increased so that pmolar levels of analyte could be measured at neutral pH.

Thus, despite the considerable research in this field, there remains a need for a simple, highly sensitive peroxidase chemiluminescent detection system that works at neutral pH, has low background in the presence of an oxidant and does not require oxygen for light generation.

SUMMARY OF THE INVENTION

The problems noted above are solved with an aqueous composition for providing a chemiluminescent signal comprising:

a) an oxidant in an amount of from about 1 to about 10 molar, b) a low molecular weight cationic surfactant present at from about 0.05 to about 2% above its critical micelle concentration, or a cationic polymer present at from about 0.01 to about 2% by weight, c) a buffer to maintain the pH of the composition at from about 6 to about 8.5, and d) a substituted acetanilide which is present in a total amount of from about 0.05 to about 10 molar as the sole chemiluminescent signal generating reagents which provide a signal in response to the catalytic activity of peroxidase, the substituted acetanilide having the structure (I):

wherein

R¹ is hydrogen or alkyl of 1 to 4 carbon atoms,

R² is hydrogen, alkyl of 1 to 4 carbon atoms, alkoxyalkyl of 1 to 4 carbon atoms, hydroxyalkyl of 1 to 4 carbon atoms, aminoalkyl of 1 to 4 carbon atoms, haloalkyl of 1 to 4 carbon atoms, or alkenyl of 2 to 5 carbon atoms, R³ is hydrogen or alkyl of 1 to 4 carbon atoms, R⁴ and R⁵ are independently hydrogen or an electron withdrawing group having a Hammett sigma value of at least about 0.01, and R⁶ and R⁷ are independently hydrogen, halo, cyano or methyl, provided that at least one of R⁴ and R⁵ is an electron withdrawing group having a Hammett sigma value of at least about 0.01, and further provided that the composition is substantially free of any other chemiluminescent agent.

This invention also provides a diagnostic test kit for the determination of an analyte catalytically related to peroxidase, the kit comprising, in individual packaging:

i) the aqueous composition as described above, and ii) a peroxidase or a peroxidase-labeled specific binding species.

Further, this invention provides a test device for the detection of peroxidase or an analyte catalytically related to peroxidase, the test device comprising an absorbent carrier material, and containing:

the low molecular weight cationic surfactant or cationic polymer as described above, the buffer as described above, and the substituted acetanilide as described above, provided that the element is substantially free of any other chemiluminescent agent.

Still further, this invention provides a method for producing a detectable signal in response to peroxidase comprising:

A) reacting a peroxidase in the presence of the aqueous composition described above, to produce a detectable chemiluminescent signal, and B) determining the resulting chemiluminescent signal as a measure of peroxidase.

This invention also provides a specific binding assay for the determination of a specific binding ligand comprising:

A) forming a peroxidase-labeled specific binding complex of a specific binding ligand with a receptor specific for the ligand, B) after separating uncomplexed materials from the peroxidase-labeled specific binding complex, contacting the peroxidase-labeled specific binding complex with the aqueous composition described above to produce a detectable chemiluminescent signal, and C) determining the resulting chemiluminescent signal as a measure of the specific binding ligand.

The present invention provides a simplified chemiluminescent detection system for peroxidase using any of certain substituted acetanilides as the chemiluminescing agent instead of conventional reagents. This system enables the user to detect pmolar levels of the peroxidase in solution or using dry analytical elements at relatively neutral pH, and thus provides high sensitivity. Low background in the absence of peroxidase is also observed with use of the practice of this invention.

DETAILED DESCRIPTION OF THE INVENTION

The present invention can be practiced to advantage in any analytical method designed to generate a chemiluminescent signal in response to the presence of a peroxidase. Such assays can involve the detection of an organic or inorganic peroxide (such as hydrogen peroxide) or peroxidase (in its free form), or the detection of a non-immunological analyte other than peroxidase or hydrogen peroxide. In particular, the invention is useful in the practice of specific binding assays which generate a chemiluminescent signal.

The assay can be qualitative or quantitative or both, and can be used to detect a biological or chemical substance (that is, an analyte) in aqueous liquids, including human or animal biological fluids, waste fluids, foods, environmental effluent, chemical processing liquids and other specimens readily apparent to one skilled in the art. In particular, the assay can be used to detect an analyte in human or animal biological fluids, including but not limited to whole blood, serum, plasma and urine.

Hydrogen peroxide (or another peroxide) can be determined with this invention. In addition, the invention can be used to determine analytes which are capable of producing hydrogen peroxide, that is, analytes which participate in one or more reactions to produce hydrogen peroxide in the presence of suitable signal generating reagents and a peroxidase. Such analytes are considered herein as "analytes catalytically related to peroxidase".

In a preferred embodiment, the invention is useful for the determination of a specific binding ligand, or its corresponding receptor (that is, a substance which specifically binds with the ligand). Such ligands include, but are not limited to, antibodies and other proteins (including lipoproteins, blood proteins, enzymes and glycoproteins), haptens, drugs, hormones, steroids, toxins, viruses, bacteria, vitamins, saccharides (including polysaccharides), immune system modulators (such as interleukins), lipids, nucleic acids, nonproteinaceous blood components, or any components thereof readily understood by one skilled in the art.

A critical component of the chemiluminescent signal generating aqueous composition of this invention is one or more substituted acetanilides of the structure (I) defined below. These compounds are the sole chemiluminescent signal generating reagents used in the practice of this invention. In other words, the compositions, test kits, test devices and methods are substantially free of all other potential chemiluminescent signal generating reagents. By "substantially free" is meant that such reagents are either not present at all, or present in such low amounts that any signal they generate is not observable over the background signal.

Thus, in the practice of this invention, the use of various other conventional chemiluminescent generating compounds can be avoided. For example, luminol and similar 2,3-dihydro-1,4-phthalazinedione derivatives are avoided with the present invention.

The compounds used to generate a light signal are defined by the structure (I):

wherein $R^1$ is hydrogen or alkyl of 1 to 4 carbon atoms (such as methyl, ethyl, isopropyl, hydroxymethyl, aminomethyl and methoxymethyl). Preferably, $R^1$ is hydrogen or methyl, and more preferably, it is hydrogen.

$R^2$ is hydrogen, alkyl of 1 to 4 carbon atoms (such as methyl, ethyl, isopropyl, t-butyl and isobutyl), alkoxyalkyl of 1 to 4 carbon atoms (such as methoxymethyl and methoxyethyl), hydroxyalkyl of 1 to 4 carbon atoms (such as hydroxymethyl, 1-hydroxyethyl, 2-hydroxyethyl and 2,3-dihydroxypropyl), aminoalkyl of 1 to 4 carbon atoms (such as aminomethyl, 2-aminoethyl, 3-aminopropyl, 2,4-diaminobutyl, methylaminomethyl, 2,2-dimethylaminoethyl and 4-aminobutyl), haloalkyl of 1 to 4 carbon atoms (such as chloromethyl, bromomethyl, 2-chloroethyl, 1,1-dichloromethyl, 1,1,1-trichloromethyl, 2,2,2-trichloroethyl and 3-chloropropyl), or alkenyl of 2 to 5 carbon atoms (such as ethenyl, 1-propenyl, isopropenyl and 2-butenyl). Preferably, $R^2$ is hydrogen, methyl, methoxymethyl, hydroxymethyl, chloromethyl or ethenyl. More preferably, it is hydrogen or methyl with methyl being most preferred.

$R^3$ is hydrogen or alkyl of 1 to 4 carbon atoms (such as methyl, ethyl, isopropyl, t-butyl, n-butyl and isobutyl). Preferably, $R^3$ is hydrogen or methyl and more preferably, it is hydrogen.

$R^4$ and $R^5$ are independently hydrogen or an electron withdrawing group having a Hammett sigma value of at least about 0.01, and preferably at least about 0.3, provided that at least one of the two radicals is an electron withdrawing group.

Hammett sigma values are calculated in accordance with standard procedures described, for example, in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (fluoro, bromo, chloro or iodo), trihalomethyl (for example, trifluoromethyl or trichloromethyl), carbonyl, carbamoyl, sulfonyl, sulfamoyl, esters, and others readily apparent to one skilled in the art. Preferred electron withdrawing groups are halo (such as chloro or bromo) and cyano. Chloro, bromo and cyano are more preferred electron withdrawing groups, and chloro or bromo is most preferred for either of $R^4$ and $R^5$.

$R^6$ and $R^7$ are independently hydrogen, methyl, cyano or halo (such as chloro or bromo). Preferably, either or both substituents are hydrogen, methyl or chloro, and most preferably, both are hydrogen.

Representative electron transfer agents having structure (I) include:
3'-chloro-4'-hydroxyacetanilide,
3',5'-dichloro-4'-hydroxyacetanilide,
2'-methyl-3'-chloro-4'-hydrocyacetanilide,
2',3'-dichloro-4'-hydroxyacetanilide,
2',5'-dichloro-4'-hydroxyacetanilide,
3'-fluoro-4'-hydroxyacetanilide,
3',5'-difluoro-4'-hydroxyacetanilide,
3'-bromo-4'-hydroxyacetanilide,
3',5'-dibromo-4'-hydroxyacetanilide,
3'-chloro-4'-hydroxy-6'-methylacetanilide,
3'-cyano-4'-hydroxyacetanilide,
3',5'-dicyano-4'-hydroxyacetanilide,
N-methyl-N-(3-chloro-4-hydroxyphenyl)acetamide,
N-(3-chloro-4-hydroxyphenyl)methacrylamide,
N-(3-chloro-4-methoxyphenyl)acetamide,
N-(3-chloro-4-hydroxyphenyl)-2-chloroacetamide,
N-(3-chloro-4-hydroxyphenyl)-2,2-dichloroacetamide,
N-(3-chloro-4-hydroxyphenyl)-2,2,2-trichloroacetamide,
N-(3-chloro-4-hydroxyphenyl)-2-hydroxyacetamide,
N-(3-chloro-4-hydroxyphenyl)-2-methoxyacetamide, and
N-(3-chloro-4-hydroxyphenyl)-2-aminoacetamide.

The most preferred compounds are 3'-chloro-4'-hydroxyacetanilide and 3'-bromo-4'-hydroxyacetanilide.

Some of these compounds are commercially available. Others can be prepared generally from known starting materials as follows:

The halogenated compounds of Structure (I) are prepared by halogenation of the known precursor anilide (for example, 4'-hydroxy- or alkoxyacetanilide) with a known halogenating agent such as sulfuryl chloride, sulfuryl bromide, or the free halogen in the presence of acid. Where the desired precursor is not available, an appropriately substituted phenol can be nitrated by mild nitration using known techniques (for example, with nitric acid in a solvent such as glacial acetic acid) followed by hydrogenation, typically over platinum or palladium to produce the amine (see *J.Am.Chem.Soc.* 49, 1093, 1927). The amine is then acylated, for example, by condensation with the desired acylating agent such as an anhydride (for example, acetic anhydride) or an acid chloride such as acrylic acid chloride, to produce the anilide. Suitable acylation procedures are also described by Challis et al, *The Chemistry of Amides*, pp. 731–857, Intersciences Publishing, New York, 1970. If the selected starting materials do not already provide the requisite electron withdrawing groups, the resulting anilide can be conveniently halogenated as described above. Alternatively, the amine precursor to the anilide can be acylated with an acylating agent that provides the group at $R^2$ (for example, trichloroacetic acid chloride or maleic anhydride), or the aromatic ring of the anilide can be alkylated, acylated or nitrated at the $R^4$ or $R^5$ (or both) positions using known techniques to provide the requisite electron withdrawing groups from $R^4$ and $R^5$.

A second component of the aqueous composition of this invention is a low molecular weight cationic surfactant to provide micelles, or a cationic polymer to provide a hydrophobic environment for increased sensitivity, storage stability and kinetic stability.

Surfactants are generally compounds which lower the surface tension of water, as is well understood by one skilled in the art. Generally, such materials are synthetic, but some are naturally occurring. Cationic surfactants have a net positive charge and are described in a number of publications including, for example, *Surfactants and Interfacial Phenomena*, By Milton J. Rosen, John Wiley and Sons, N.Y., 1978, pages 13–17 and are identified by tradenames in *McCutcheon's Emulsifiers and Detergents*, North American Ed., McCutcheon's Division, The Manufacturing Confectioner Publishing Co., 1988, page 259. Positive charges in the surfactants can be provided by cationic groups including, but not limited to, quaternary ammonium, quaternary phosphonium, sulfonium, pyridinium, pyrimidinium, imidazolium and oxonium.

Particularly useful cationic surfactants and polymers can be represented by the structure (II):

wherein $R^8$ is substituted or unsubstituted alkyl of at least 7 carbon atoms, and preferably from 10 to 20 carbon atoms (such as n-octyl, isononyl, isodecyl, dodecyl, tetradecyl, hexadecyl, octadecyl, eicosyl, 2,7,8-trimethyldecyl, 4-ethyl-6-methyldodecyl, benzyl and phenethyl), substituted or unsubstituted aryl of 6 to 14 carbon atoms in the aromatic nucleus (such as phenyl, naphthyl or anthryl) which can be substituted with one or more hydrophobic groups such as linear or branched alkyl of 1 to 10 carbon atoms (such as methyl, ethyl, isopropyl, t-butyl, hexyl, octyl, isooctyl, nonyl or isononyl), halo and others known to one skilled in the art. Such substituted aryl groups include, but are not limited to xylyl, tolyl, isononylphenyl, dimethylphenyl and trichlorophenyl. $R^8$ can also be substituted or unsubstituted alkenyl of 8 to 20 carbon atoms (such as 1-octenyl, 1-decenyl and 2-dodecenyl), or a polymeric moiety (described below).

Preferably, $R^8$ is alkyl or alkenyl of 14 to 16 carbon atoms, with groups such as 2,4-dimethyl-6-ethyldecyl, tetradecyl and hexadecyl being more preferred.

In structure (II), $R^9$ can be alkyl or alkenyl as defined for $R^8$, substituted or unsubstituted alkyl of 1 to 7 carbon atoms (such as methyl, ethyl, isopropyl, t-butyl, methoxymethyl, benzyl and hexyl), substituted or unsubstituted alkenyl of 2 to 7 carbon atoms (such as ethenyl, allyl, isopropenyl and n-butenyl), or carbocyclic aryl of 6 to 10 carbon atoms in the ring system (such as phenyl, tolyl, xylyl, naphthyl and p-methoxyphenyl).

$R^{10}$ and $R^{11}$ are independently substituted or unsubstituted alkyl of 1 to 7 carbon atoms (such as methyl, ethyl, isopropyl, t-butyl, methoxymethyl, benzyl and hexyl), substituted or unsubstituted alkenyl of 2 to 7 carbon atoms (such as a ethenyl, isopropenyl and allyl), or carbocyclic aryl of 6 to 10 carbon atoms in the ring system (such as phenyl, tolyl, xylyl, naphthyl and p-methoxyphenyl).

Alternatively, any two or three of $R^9$, $R^{10}$ and $R^{11}$ can be taken together to represent sufficient carbon atoms and an oxygen, nitrogen or sulfur atom to complete, with the quaternary ammonium atom, a 5- to 6-membered heterocyclyl cationic group. Examples of such groups include, but are not limited to pyridinium, piperidinium, pyrrolidinium, morpholinium, quinolinium, pyrimidinium, acridinium, benzothiazolium, benzoxazolinium and imidazolium.

Preferably, $R^9$, $R^{10}$ and $R^{11}$ are independently methyl or ethyl.

$Y^-$ is a suitable monovalent acid anion which is not a substrate or inhibitor for peroxidases, including but not limited to, perchlorate, halide (such as fluoride, chloride and bromide), tetrafluoroborate, triflate, methyl sulfate, hexafluorophosphate, nitrate, p-toluenesulfonate and others readily apparent to one skilled in the art. Halide anions are preferred.

Examples of useful nonpolymeric cationic surfactants are hexadecyltrimethylammonium chloride, dodecyltrimethylammonium chloride, cetyltrimethylammonium bromide (also known as hexadecyltrimethylammonium bromide), cocotrimethylammonium chloride, tallowtrimethylammonium chloride, soyatrimethylammonium chloride, myristyltrimethylammonium bromide, stearyltrimethylammonium chloride, cetylethyldimethylammonium bromide, didodecyldimethylammonium bromide, cetylpyridinium chloride and myristyldimethylbenzylammonium chloride.

Cetyltrimethylammonium bromide and cetyltrimethylammonium chloride are most preferred.

Many of these surfactants are readily available from a number of commercial sources. Others can be readily prepared by a skilled chemist using known starting materials and procedures.

Where $R^8$ in structure (II) is a polymeric moiety, the backbone of such polymers can be conventional polyesters, polyamides, polyethyleneimines, polycarbonates, cellulosic materials, and vinyl addition homo- and copolymers comprised of recurring units of a monomer having the desired positive charge. These materials can be prepared from conventional materials using conventional procedures. The polymer can have the charges incorporated therein from starting materials, or from chemical reaction after preparation.

Particularly useful cationic polymers are vinyl addition homo- or copolymers prepared from ethylenically unsaturated polymerizable monomers having the requisite positively charged groups, and one or more comonomers which provide hydrophobic regions characteristic of surfactants, crosslinked regions or other suitable properties.

Representative cationic monomers include, but are not limited to; N-cyclohexyl-N,N-dimethyl-N-(m- & p-vinylbenzyl)ammonium chloride, N-benzyl-N,N-dimethyl-N-(m- & p-vinylbenzyl)ammonium chloride, 3-(2-hydroxypropyl)-1-vinylimidazolium chloride and 1-methyl-4-vinylpyridinium chloride. Useful comonomers include, but are not limited to, styrene and its derivatives (such as vinyltoluene and p-t-butylstyrene), acrylic and methacrylic acid esters (such as methyl acrylate, methyl methacrylate, butyl acrylate and butyl methacrylate), crosslinkable monomers {such as divinylbenzene, ethylene diacrylate, ethylene dimethacrylate and N,N'-methylenebis(acrylamide)]. Other useful polymers are described, for example, as mordants in U.S. Pat. No. 4,069,017 (Wu et al) and U.S. Pat. No. 4,024,839 (Wu et al). Such materials generally have quaternary ammonium or quaternary phosphonium groups pendant from the polymer backbone, and preferably at least from about 40 to 100 weight percent of the ethylenically unsaturated polymerizable monomer derived recurring units have such groups. The remaining recurring units can be derived from a wide variety of ethylenically unsaturated polymerizable monomers as noted in the patents identified above.

Representative cationic polymers include, but are not limited to, poly(N,N,N-trimethyl-N-vinylbenzylammonium chloride), poly[styrene-co-benzyl-N,N-dimethyl-N-(m- & p-vinylbenzyl)ammonium chloride-co-divinylbenzene], poly(N,N,N-trioctyl-N-vinylbenzylphosphonium chloride), poly[styrene-co-N-vinylbenzyl-N,N,N-trihexylammonium chloride], poly(styrene-co-N,N,N-trimethyl-N-vinylbenzylammonium chloride) , poly[N-cyclohexyl-N,N-dimethyl-N-(m- & p-vinylbenzyl)ammonium chloride], poly[styrene-co-1-vinylimidazole-co-3-(2-hydroxyethyl)-

1-vinylimidazolium chloride] and others readily apparent to one skilled in the art. A preferred cationic polymer is poly[N-cyclohexyl-N,N-dimethyl-N-(m- & p-vinylbenzyl) ammonium chloride].

The signal-providing composition of this invention is generally buffered to a pH of from about 6 to about 8.5 (preferably from about 6.5 to about 8) using one or more suitable buffers well known in the art. For example, buffers such as tris(hydroxymethyl)aminomethane, bis(2-hydroxyethyl)iminotris(hydroxymethyl)methane, N,N-bis(2-hydroxyethyl)-2-aminoethanesulfonic acid, 1,3-bis[tris(hydroxymethyl)methylamino]propane, N-(2-hydroxyethyl)piperazine-N'-(3-propanesulfonic acid), N-(2-hydroxyethyl)piperazine-N'-(2-ethanesulfonic acid) and phosphate can be used. Tris(hydroxymethyl)aminomethane is preferred. As used to define pH, the term "about" refers to ±0.2 units.

An oxidant is needed in the practice of this invention to cause excitation of the substituted acetanilide so that light is emitted in the presence of a peroxidase. Various useful oxidants are known, but perborate ion and hydrogen peroxide are preferred with the latter being most preferred.

Various optional addenda which can be included in the aqueous composition of this invention are chelating agents, various inorganic salts for ionic strength (such as sodium chloride and potassium chloride and stabilizers such as sodium benzoate.

In the aqueous signal-providing composition of this invention, the amounts of each component can be varied depending upon where it is intended for use, the particular sensitivity of the reagents and other factors well understood by one skilled in the art. Thus, the following general ranges are meant to provide guidance for the skilled worker, and not to limit the practice of this invention.

The amount of oxidant is generally at least about 1 molar, with an amount in the range of from about 1 to about 10 mmolar being preferred. The substituted acetanilide of structure (I) is generally present in an amount of at least about 0.05 mmolar, with an amount in the range of from about 0.05 to about 10 mmolar being preferred. The cationic surfactant is generally present in an amount of from about 0.05 to about 2% above the critical micelle concentration, and when the cationic polymer is used, it is generally present in an amount of from about 0.01 to about 2%, by weight. The amount of buffer can vary depending upon the buffer used, but generally it is from about 0.01 to about 0.3 molar. As used herein to define concentrations, the term "about" refers to ±10% of the indicated value.

The "critical micelle concentration" for many surfactants is well known, or it can be readily determined using procedures described, for example, in *Surfactant Science and Technology*, Meyers, VCH Publishers, New York, Chapter 3, 1988.

This invention also provides a peroxidase-containing aqueous composition as part of a kit, which composition contains a peroxidase in free form, or as a label conjugated with a specific binding molecule (such as an antibody, avidin or biotin). Such a composition can also be buffered as described above for the signal-providing composition of this invention. The amounts of peroxidase or peroxidase-labeled specific binding molecule present in this composition would be readily apparent to one skilled in the art.

Besides the compositions described above, the kit can also include other individually packaged reagents, equipment and instructions useful for carrying out a variety of analytical methods (described below). The packaging of kit components is well known in the art.

As used herein, "peroxidase" is meant to be any peroxidative substance (enzymatic or otherwise) which catalyzes the oxidation of a substrate, that is the substituted acetanilide described herein, to produce the appropriate emission of light. Microbial, fungal and plant peroxidases are preferred with horseradish peroxidase being most preferred. The amount of peroxidase can vary widely due to the amount of other components used in the reaction. A useful amount would be readily apparent to one skilled in the art, but a minimum amount would generally be at least about $1 \times 10^{-7}$ I.U./ml (or an equivalent amount for nonenzymatic peroxidative substances). I.U. represents the International Unit for enzyme activity and is defined as the amount of enzyme activity required to catalyze the conversion of 1 micromole of substrate to product per minute under standard conditions.

In specific binding methods, the peroxidase is used as a conjugate with a specific binding ligand or receptor therefor, or with a specific binding molecule which is reactive with either the ligand or receptor. The ligand and receptor are complexed in such assays and thereby labeled with the peroxidase for eventual detection of the labeled complex or labeled uncomplexed materials. The preparation of such conjugates can be achieved using a variety of known techniques (for example, as described by Yoshitake et al, *Eur.J.Biochem.*, 101, 395, 1979, and in U.S. Pat. No. 5,106,732 of Kondo et al).

Various specific binding assay formats are useful in the practice of this invention, and include nucleic acid hybridization assays, immunochemical assays (such as enzyme immunoassays, sandwich assays, competitive binding assays, direct binding assays) and others well known in the art. Such assays are generally described, for example in U.S. Pat. No. 4,598,044, U.S. Pat. No. 4,745,077 (Holian et al), U.S. Pat. No. 5,077,198 (Shih et al), U.S. Pat. No. 5,085,986 (Mauck et al), Matthews et al, *Anal.Biochem.* 169, pages 1–25 (1988), and WO 88/01302 (published Feb. 25, 1988). The method of the invention can be preceded by an amplification process, such as polymerase chain reaction (commonly known as PCR) as described for example in U.S. Pat. No. 4,965,188 (Mullis et al) and ligase chain reaction which is generally described by Weiss, *Science*, 254, pages 1292–3, 1991 to increase the amount of targeted nucleic acid which can then be detected using the composition of this invention.

Particularly useful specific binding methods of this invention are those known in the art as sandwich assays whereby the ligand of interest is complexed with at least a first and second receptor either simultaneously or in a desired sequence. One of the receptors is a capture reagent which is either insolubilized on a suitable support (such as microtiter plate, polymeric, magnetic or glass particles, film, membrane, filter paper and other materials known in the art) by adsorption, covalent or other known attachment procedures, or is capable of being insolubilized through further complexation or reaction. For example, the capture reagent can be labeled with a specific binding moiety (for example, biotin) which is reactive with its corresponding receptor moiety (for example, avidin) which is insolubilized on a support.

In the sandwich assays, the second receptor for the ligand of interest is a detection reagent which can be labeled with a peroxidase, or is capable of being so labeled through additional specific binding reactions (such as through an avidin-biotin complex). Detection of the label is accomplished using the composition of this invention.

In more preferred embodiments, the ligand of interest is an antigenic material with which antibodies are reactive, or a nucleic acid with which complementary nucleic acids (such as oligonucleotides) can be hybridized. Other embodiments include competitive binding assays wherein a specific binding ligand of interest competes with a peroxidase-labeled analogue of the ligand for a single receptor.

The assays described above can be carried out in solution or in a dry format. Solution assays generally refer to methods carried out in solution in a suitable container, and in the case of heterogeneous specific binding assays, suitable separation techniques and equipment are then used to separate unbound materials from the bound materials. In dry assays, chemical or specific binding reactions can be carried out in a dry element, test strip or fibrous sheet and the presence of the analyte is detected within the element upon reaction by the various reagents when a test specimen is applied to the element or test device. Details regarding such elements are well known in the art, including for example, U.S. Pat. No. 3,992,158 (Przybylowicz et al), U.S. Pat. No. 4,258,001 (Pierce et al), U.S. Pat. No. 4,292,272 (Kitajima et al), U.S. Pat. No. 4,430,436 (Koyama et al) and U.S. Pat. No. 4,670,381 (Frickey et al), incorporated herein by reference.

Generally, the elements comprise at least an absorbent carrier material, and optionally additional reagent layers or zones. The reagents useful in the present invention can be in the same or different layers or zones of the element.

The following examples are provided to illustrate the practice of this invention, but are not intended to be limiting. All percentages are by weight, unless otherwise noted.

Except where noted, all reagents and equipment were obtained from Eastman Kodak Company or other commercial sources.

The following preparations describe representative procedures for making some of the substituted acetanilides useful in the practice of this invention.

Preparation A:

Into a 1 liter round bottom flask (fitted with a magnetic stirrer), glacial acetic acid (700 ml) was mixed with 4'-hydroxyacetanilide (50 g) until the solid was completely dissolved. The resulting solution was cooled to between 10°–15° C., and to it was added $SO_2Cl_2$ (47 g) and the resulting solution was stirred for 1 hour. Water (200 ml) was then added, and 3'-chloro-4'-hydroxyacetanilide was crystallized as a white precipitate (60 g, 98% yield).

Preparation B:

Into a 500 ml round bottom flask (fitted with a magnetic stirrer), water (200 ml) was mixed with 4-amino-2,6-dichlorophenol hydrochloride (20 g) until the solid was completely dissolved. The resulting solution was warmed to 70° C., and to it was added acetic anhydride (11 g) and the resulting solution was stirred for 1 hour. Upon cooling, crystals of 3',5'-dichloro-4'-hydroxyacetanilide were formed (19.6 g, 95% yield).

EXAMPLES 1–4

Aqueous Chemiluminescent Compositions

Aqueous compositions of this invention for providing a chemiluminescent signal were prepared by mixing cetyltrimethylammonium chloride (0.1%), hydrogen peroxide (3 mmolar), and various chemiluminescent agents (1 mmolar) in tris(hydroxymethyl)aminomethane hydrochloride buffer (0.05 molar, pH 7.2). Several Control compositions were similarly prepared to include known fluorescent dyes. Signal generation was measured at 37° C. using a conventional Turner TD-20e luminometer when various amounts of horseradish peroxidase (Sigma Chemical XII) were mixed with the compositions (final volume of 200 µl).

As chemiluminescent agents, Example 1 contained 3'-chloro-4'-hydroxyacetanilide, Example 2 contained 3'-fluoro-4'-hydroxyacetanilide, Example 3 contained 2'-methyl-3'-chloro-4'-hydroxyacetanilide, and Example 4 contained 3'-bromo-4'-hydroxyacetanilide.

Control A contained fluorescein, Control B contained eosin Y, and Control C contained coumarin 343.

Table I below shows the average light signals generated by the compositions for three replicates in each experiment (10 second integral light units at t=4 minutes) after addition of peroxidase. The "signal to noise" ratio (S/N) is the ratio of the light signal generated by the composition in the presence of horseradish peroxidase to the signal generated from background (no peroxidase).

TABLE I

| Peroxidase Level (pmolar) | Example 1 | | Example 2 | | Example 3 | | Example 4 | |
|---|---|---|---|---|---|---|---|---|
| | Signal | S/N | Signal | S/N | Signal | S/N | Signal | S/N |
| 0 | 0.008 | 1.0 | 0.012 | 1.0 | 0.007 | 1.0 | 0.007 | 1.0 |
| 0.1 | 0.010 | 1.25 | 0.060 | 5.0 | — | — | — | — |
| 1 | 0.080 | 10 | 0.410 | 34 | 0.050 | 7.1 | 0.010 | 14 |
| 10 | 1.25 | 156 | 3.80 | 317 | 0.080 | 11 | 0.72 | 103 |
| 100 | 61.40 | 7675 | 10.56 | 880 | 0.69 | 99 | 16.56 | 2366 |

| Peroxidase Level (pmolar) | Control A | | Control B | | Control C | |
|---|---|---|---|---|---|---|
| | Signal | S/N | Signal | S/N | Signal | S/N |
| 0 | 1.51 | 1.0 | 0.227 | 1.0 | 0.006 | 1.0 |
| 0.1 | — | — | — | — | — | — |
| 1 | — | — | — | — | — | — |
| 10 | 0.64 | 0.4 | — | — | — | — |
| 100 | 0.70 | 0.46 | 0.17 | 0.75 | 0.06 | 10 |

The results in Table I indicate that the compositions of this invention exhibit low background and high sensitivity in the presence of horseradish peroxidase, even at the 1 pmolar concentration of the enzyme. The Control compositions exhibited either high background (Controls A and B) or unacceptably low S/N ratio (Control C), or both at the 100 pmolar enzyme level.

EXAMPLE 5

Preferred Aqueous Chemiluminescent Composition

A preferred aqueous composition of this invention was prepared by mixing diethylenetriaminepentaacetic acid (100

μmolar), hydrogen peroxide (2 mmolar), cetyltrimethylammonium bromide (0.1%) and 3'-chloro-4'-hydroxyacetanilide (0.5 mmolar) in tris(hydroxymethyl) aminomethane hydrochloride (0.05 molar, pH 8). Controls D, E and F were similarly prepared but contained 4'-hydroxyacetanilide (0.5 mmolar), 4-iodophenol (1 mmolar) and 4'-hydroxycinnamic acid (0.5 mmolar) instead of the substituted 4'-hydroxyacetanilide. The final volume of each reaction mixture was 200 μl after addition of various concentrations of horseradish peroxidase (Sigma Chemical XII).

Table II below lists the average light signal (10 second integrals at t=5 minutes) data of 3 replicates obtained using a conventional Turner TD-20e luminometer at 37° C. The present invention exhibits greater sensitivity than compositions containing prior art compounds.

TABLE II

| Peroxidase Level (pmolar) | Example 5 | Control D | Control E | Control F |
| --- | --- | --- | --- | --- |
| 25 | 3.85 | 0.076 | 2.28 | 0.48 |
| 250 | 68.6 | 10.16 | 16.2 | 1.21 |
| 2500 | 112.7 | 48.12 | 93.9 | 9.50 |

EXAMPLE 6

Comparative Example

This example compares the present invention with compositions prepared using chemiluminescent agents described in the prior art.

A composition of this invention (Example 6) was prepared by mixing diethylenetriaminepentaacetic acid (10 μmolar), hydrogen peroxide (3 mmolar), cetyltrimethylammonium chloride (0.1%) and 3'-chloro-4'-hydroxyacetanilide (1 mmolar) in tris(hydroxymethyl) aminomethane hydrochloride (0.05 molar, pH 7.2). Example 6a was carried out using the same composition, but on a different day.

Control compositions G and H contained purpurogallin (Sigma Chemical) (0.2 mmolar), ethanol (25% for Control G and 5% for Control H), hydrogen peroxide (12.5 mmolar) and chelating agent (10 μmolar) in phosphate buffer (0.01 molar, pH 6.5). Control compositions I and J were prepared like the composition of this invention except they contained 7-hydroxycoumarin or esculin monohydrate, respectively as chemiluminescent agents (each at 1 mmolar).

Table III below lists the average signal data obtained for three replicates when various amounts of horseradish peroxidase were added using the procedure and equipment described in Examples 1–4. The final volume for each reaction mixture was 200 μl.

TABLE III

| Peroxidase Level (pmolar) | Example 6 | | Control G | | Control H | |
| --- | --- | --- | --- | --- | --- | --- |
| | Signal | S/N | Signal | S/N | Signal | S/N |
| 0 | 0.00033 | 1 | 0.590 | 1 | 0.339 | 1 |
| 0.5 | 0.036 | 107 | 0.662 | 1.1 | 0.405 | 1.2 |
| 5.0 | 0.582 | 1747 | 0.835 | 1.4 | 0.61 | 1.8 |
| 500 | 381 | 1.143 million | 6.04 | 10.2 | 10.51 | 31 |
| 1000 | 143 | 0.43 million | 56.8 | 96.3 | 18.13 | 53 |

TABLE III-continued

| Peroxidase Level (pmolar) | Example 6a | | Control I | | Control J | |
| --- | --- | --- | --- | --- | --- | --- |
| | Signal | S/N | Signal | S/N | Signal | S/N |
| 0 | 0.005 | 1 | 0.036 | 1 | 0.024 | 1 |
| 0.5 | — | — | — | — | — | — |
| 5.0 | — | — | — | — | — | — |
| 50 | 18.23 | 3646 | 1.79 | 49.7 | 0.019 | 0.8 |
| 500 | — | — | — | — | — | — |
| 1000 | — | — | — | — | — | — |

EXAMPLE 7

Background Comparisons

This example demonstrates that the aqueous composition of the present invention exhibits low background signal compared to compositions of the prior art.

A composition of the present invention was prepared by mixing 3'-chloro-4'-hydroxyacetanilide (1 molar), cetyltrimethylammonium chloride (0.1%), diethylenetriaminepentaacetic acid (10 μmolar) and hydrogen peroxide (3 molar) in tris(hydroxymethyl)aminomethane hydrochloride buffer (0.05 molar, pH 8.5).

A Control K composition was like the composition of this invention except that it contained fluorescein as the chemiluminescent agent and had a pH of 7.2, and Control L was similar to Control K except that it contained eosin Y instead of fluorescein. Control M was like the composition of this invention except that it also contained luminol (1 mmolar) and had a pH of 8. Commercially available AMERLITE™ Signal Generating Reagent containing luminol (0.2 mmolar) and p-iodophenol (0.25 mmolar) in sodium perborate buffer (1 mmolar, pH 8.5) was compared as Control N.

Table IV below lists the average background signal and standard deviations obtained from three replicates using a Turner TD-20e luminometer at 37° C. (10 second integrals). The reaction mixture volume for each composition was 200 μl.

TABLE IV

| Composition | Average Background Signal | Standard Deviation |
| --- | --- | --- |
| Example 7 | 0.018 | 0.025 |
| Control K | 1.76 | 0.38 |
| Control L | 0.272 | 0.05 |
| Control M | 0.097 | 0.013 |
| Control N | 7.24 | 1.215 |

These results indicate that the composition of this invention exhibits essentially zero background in the absence of a peroxidase while many known chemiluminescent compositions exhibit observable background.

EXAMPLE 8

Detection of Fungal Peroxidase

This example demonstrates the usefulness of the present invention to detect a fungal peroxidase, so that it is clear that the invention is not limited to a particular peroxidase in its practice.

A composition of this invention was prepared by mixing 3'-chloro-4'-hydroxyacetanilide (1 molar), diethylenetriaminepentaacetic acid (10 μmolar), cetyltrimethylammonium chloride (0.1%) and hydrogen peroxide (3 molar) in tris(hydroxymethyl)aminomethane hydrochloride buffer (0.05 molar, pH 7.2). Data (average of three replicates) from the detection of various amounts of peroxidase from the fungus *Arthromyces ramosus* (Sigma Chemical) was obtained using the procedure described for Examples 1–4, are listed below in Table V.

TABLE V

| Peroxidase Level (pmolar) | Signal | S/N |
|---|---|---|
| 0 | 0.005 | 1 |
| 50 | 0.34 | 68 |
| 500 | 52.77 | 10554 |

EXAMPLE 9

Comparison at Neutral pH

A composition of this invention and a composition of the prior art (Control P) were compared at various assay pH values.

The composition of this invention was prepared by mixing diethylenetriaminepentaacetic acid (10 μmolar), hydrogen peroxide (2 molar), 3'-chloro-4'-hydroxyacetanilide (1 molar) and cetyltrimethylammonium bromide (0.1%) in tris(hydroxymethyl)aminomethane hydrochloride buffer (0.2 molar).

The Control P composition contained luminol (1 molar), 4'-hydroxyacetanilide (0.15 molar), cetyltrimethylammonium bromide (0.1%), and hydrogen peroxide (2 molar) in buffer (0.05 molar).

Figure 1:
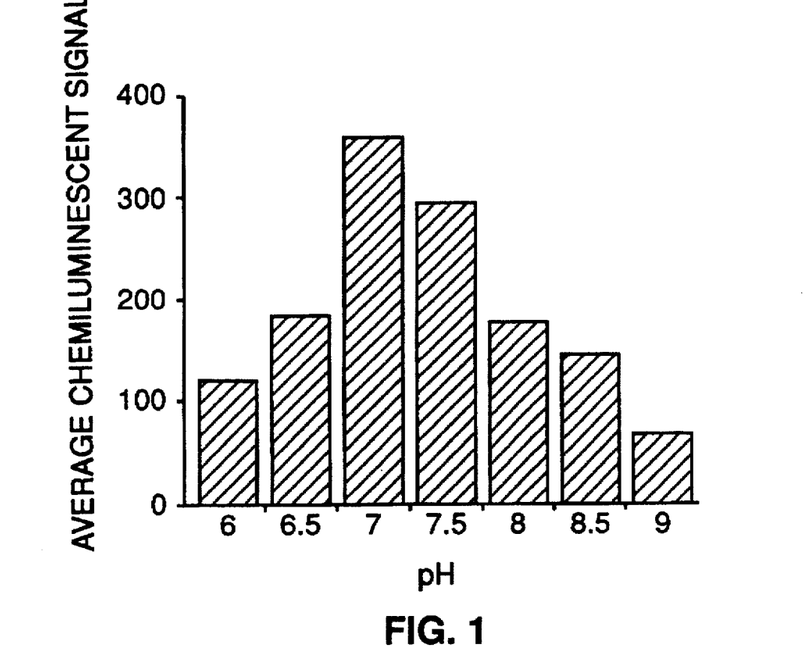
FIG. 1 is a bar graph showing chemiluminescence signal at various pH values for a composition of this invention, as described in Example 9 below.
Figure 2:
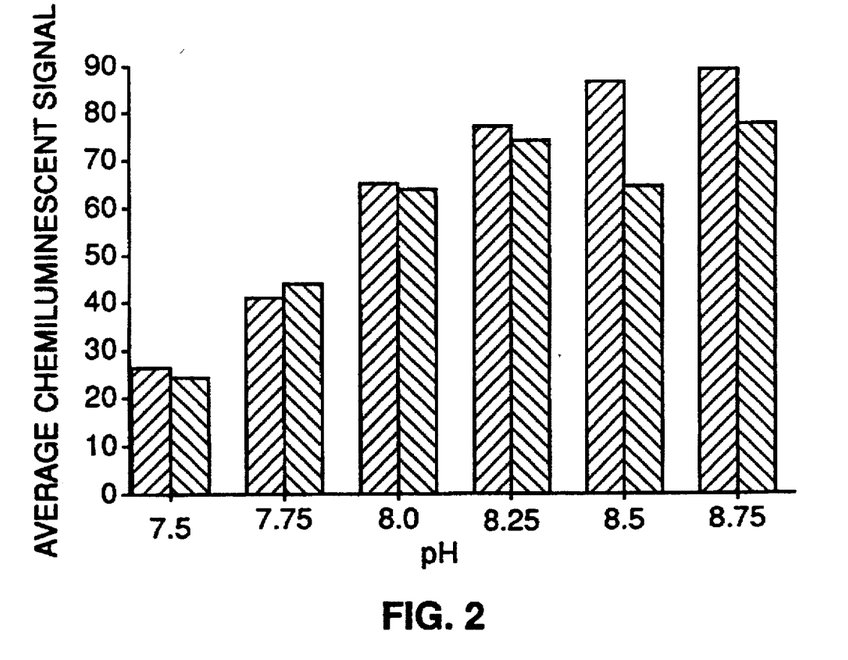
FIG. 2 is a bar graph showing chemiluminescence signal at various pH values for a Control composition, as described in Example 9 below.

Sigma Chemical XII horseradish peroxidase was added to each composition (250 pmolar for Invention, 25 pmolar for Control P) to give final reaction mixture volumes of 200 μl. The resulting signal was observed using a commercially available Luminoskan plate reader at either 25° or 37° C. (10 second integral at t=5 seconds) for Control P, and a Turner TD-20e luminometer at 37° C. (10 second integral at t=5 seconds) for the Invention. The results are from three replicates for each composition, and are illustrated in FIG. 1 for the invention and FIG. 2 for Control P. In FIG. 2, the first bar at each pH value represents the signal obtained at 25° C., and the second bar represents the signal obtained at 37° C.

It is apparent that the present invention optimally generates light near neutral pH while the Control P composition provides an optimum signal at pH 8.5–8.75.

EXAMPLE 10

Analytical Element

This example shows the preparation of a test device of this invention and its use to detect peroxidase at various concentrations using the present invention.

An aqueous composition of this invention was prepared by mixing cetyltrimethylammonium bromide (0.1%), diethylenetriaminepentaacetic acid (10 μmolar), hydrogen peroxide (2 molar) and 3'-chloro-4'-hydroxyacetanilide (1 mmolar) in tris(hydroxymethyl)aminomethane hydrochloride buffer (0.05 molar, pH 8).

A stock solution of Sigma Chemical XII horseradish peroxidase (8 μmolar) was prepared in the same buffer. This solution was serially diluted in the noted buffer to prepare solutions having various amounts of peroxidase for mixing with a composition of this invention.

Figure 3:
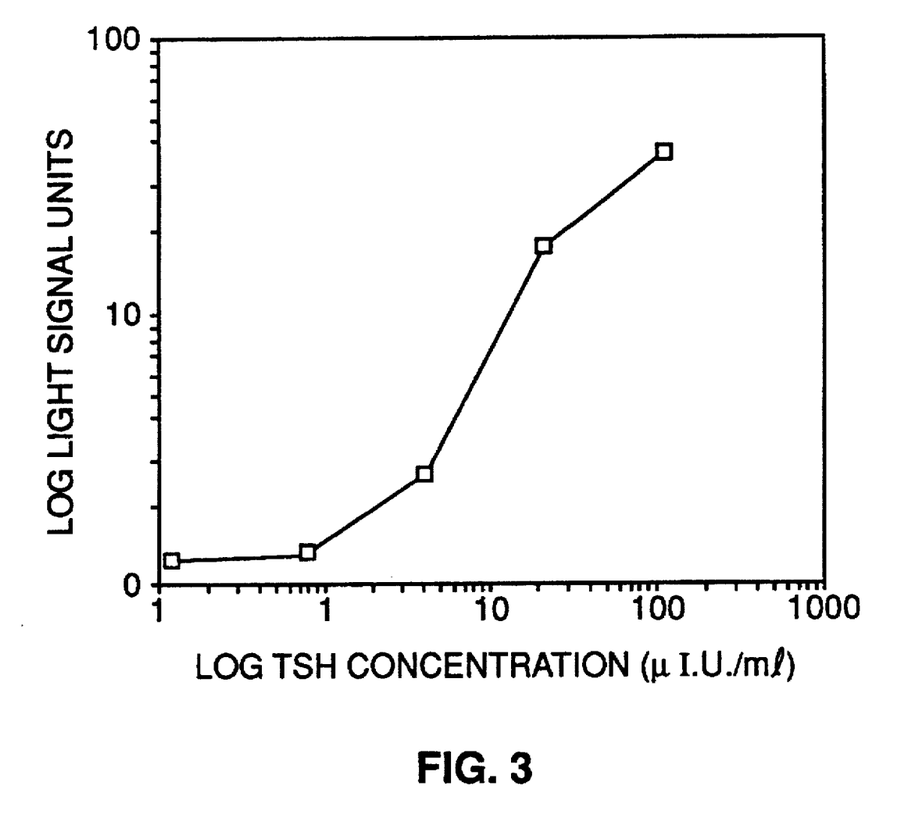
FIG. 3 is a graphical illustration of chemiluminescent signal versus log concentration of thyroid stimulating hormone (TSH) as described in Example 18 below.

Dry analytical elements were prepared having the general structure shown in FIGS. 1–3 of copending U.S. Ser. No. 07/938,460 (filed Aug. 31, 1992 by Belly et al), containing Whatman GF/B glass microfibers as the absorbing layer to provide a high wash capacity in the elements. These elements shown herein are illustrative of the present invention and not essential to its practice. Various other element structures can be similarly used.

Each prepared element had the following components in the reagent matrix which is in contact with the absorbing layer:

| Element Structure | |
|---|---|
| | g/m² |
| Porous Spreading Layer | |
| Poly(vinyltoluene-co-methacrylic acid)(98:2 weight ratio) beads | 130 |
| Poly(methyl acrylate-co-sodium 2-acrylamido-2-methylpropanesulfonate-co-2-acetoacetoxyethyl methacrylate)(90:4:6 weight ratio) | 2.583 |
| ZONYL ™ FSN fluorinated surfactant (DuPont) | 0.054 |
| Tris(hydroxymethyl)amino methane hydrochloride buffer (pH 8, 0.1 molar) | 1.211 |
| Diethylene-triaminepentaacetic acid | 0.004 |
| Binder Layer | |
| Gelatin (hardened) | 10.15 |
| Buffer (same as above, pH 8, 0.1 molar) | 1.21 |
| Diethylene-triaminepentaacetic acid | 0.004 |
| TRITON ™ X-100 nonionic surfactant (Union Carbide) | 0.02 |
| Poly(ethylene terephthalate) Support | |

The composition of this invention (100 μl) was applied to the element and allowed to soak into the absorbing layer. Another sample of the composition was mixed with a peroxidase solution in a 40:1 volume ratio, and this mixture (5 μl) was applied to the element. After a five minute incubation period at room temperature, the frame was taken off the element and the layer containing the reagents and reaction products was placed in a conventional luminometer for 5 minutes to record light emission (10 second integral).

Table VI below lists the data obtained from two replicates of each peroxidase concentration (obtained by varying the amount of peroxidase solution used in the reaction mixture). These results demonstrate the usefulness of the present invention to detect peroxidase using a dry analytical element with acceptable sensitivity and low background.

TABLE VI

| Peroxidase Level (pmolar) | Signal | S/N |
|---|---|---|
| 0 | 0.108 | 1 |
| 10 | 0.168 | 1.56 |
| 20 | 0.182 | 1.69 |
| 50 | 0.300 | 2.78 |
| 100 | 0.420 | 3.89 |
| 200 | 0.704 | 6.52 |

TABLE VI-continued

| Peroxidase Level (pmolar) | Signal | S/N |
|---|---|---|
| 1000 | 2.96 | 27.40 |
| 2000 | 4.48 | 41.48 |
| 10,000 | 7.22 | 66.38 |
| 20,000 | 7.46 | 69.07 |

EXAMPLES 11-17

Comparison of Various Cationic Surfactants

The usefulness of various cationic surfactants and cationic polymers was demonstrated by using various of these compounds in compositions of this invention, and measuring peroxidase as an analyte.

The compositions were prepared by mixing 3'-chloro-4'-hydroxyacetanilide (1 mmolar), hydrogen peroxide (3 mmolar), diethylenetriaminepentaacetic acid (10 μmolar) and the cationic material (listed below, various amounts) in tris(hydroxymethyl)aminomethane hydrochloride buffer (0.05 molar, pH 7.2).

Sigma Chemical XII horseradish peroxidase (100 pmolar) was mixed with the composition and the resulting light signals from the reaction mixture (200 μl) were measured using a Turner TD-20e luminometer at 37° C. (10 second integral at t=4 minutes). Background signals from the compositions were measured without the presence of the peroxidase.

The data obtained are listed in Table VII below as averages for 3 replicates of the Invention compositions. The background signals are the averages of 12 data points over 1 to 4 minutes. These data show that various cationic materials can be used in the compositions of the present invention because of low background and high sensitivity.

The cationic materials used are as follows:

Example 11: Cetyltrimethylammonium chloride (0.1%),

Example 12: Poly[styrene-co-N-vinylimidazole-co-3-(2-hydroxyethyl)-1-vinylimidazolium chloride] (50:40:10 molar ratio) (0.025%), Example 13: cetylpyridinium chloride (0.1%), Example 14: poly[styrene-co-N-benzyl-N,N-dimethyl-N-(m- & p-vinylbenzyl)ammonium chloride-co-divinylbenzene] (4.95:4.95:0.1 molar ratio) (0.05%), Example 15: poly[N-cyclohexyl-N,N-dimethyl-N-(m- & p-vinylbenzyl)ammonium chloride] (0.25%), Example 16: Cetyltrimethylammonium bromide (0.1%), and Example 17: poly[styrene-co-N-vinylimidazole-co-3-(2-hydroxyethyl)-1-vinylimidazolium chloride] (44:20:36 molar ratio) (0.1%).

TABLE VII

| Composition | Signal | Background Signal | S/N |
|---|---|---|---|
| Example 11 | 65.81 | 0.017 | 3890 |
| Example 12 | 1.82 | 0.009 | 202.2 |
| Example 13 | 0.30 | 0.010 | 31.0 |
| Example 14 | 4.02 | 0.016 | 248.7 |
| Example 15 | 22.53 | 0.033 | 681.0 |
| Example 16 | 60.99 | 0.017 | 3588 |
| Example 17 | 8.92 | 0.034 | 264.9 |

EXAMPLE 18

Solution Immunoassay for Thyroid Stimulating Hormone (TSH)

This example demonstrates the practice of this invention for the detection of TSH in a biological specimen. The assay was carried out using a commercially available AMERLITE™ Fast TSH immunoassay kit (Kodak Clinical Diagnostics, Ltd.), plate washer/incubator and chemiluminescence reader.

The chemiluminescent signal was generated using a composition of this invention containing 3'-chloro-4'-hydroxyacetanilide (1 mmolar), hydrogen peroxide (3 mmolar), diethylenetriaminepentaacetic acid (10 μmolar) and cetyltrimethylammonium chloride (0.1%) in tris (hydroxymethyl)aminomethane hydrochloride buffer (0.05 molar, pH 7.2).

The protocol described in the commercial AMERLITE™ Fast TSH kit noted above was followed:

1) A specimen containing 0–100 μI.U./ml of TSH was added to a test well of the kit test device containing anti-TSH monoclonal antibodies adsorbed to the walls thereof.

2) Anti-β-TSH-horseradish peroxidase conjugate of the commercial kit was added to the test well to form a ternary complex.

3) Incubation was carried out at 37° C. for about 30 minutes.

4) Unbound materials were washed from the test well using the commercial kit wash solution.

5) The solution (described above) for generating the chemiluminescent signal was then added, and the resulting signal was evaluated after 5 minutes using the "scan-only" software mode of the chemiluminescence reader.

FIG. 3 shows the signal results. Appreciable signal was generated in the presence of 4, 20 and 100 μI.U./ml TSH (last three data points). Thus, the present invention is useful for the determination of an immunological analyte.

EXAMPLES 19-21

Additional Chemiluminescent Compositions

Several aqueous compositions were prepared and tested similarly to those in Examples 1-4 above. The compositions were prepared by mixing cetyltrimethylammonium chloride (0.1%), hydrogen peroxide (3 mmolar), diethylenetriaminepentaacetic acid (10 μmolar) and various chemiluminescent agents (1 mmolar) in tris(hydroxymethyl)aminomethane hydrochloride buffer (0.05 molar, pH 7.2). Signal generation was measured at 37° C. using a conventional Turner TD-20e luminometer when various amounts of horseradish peroxidase (Sigma Chemical XII) were mixed with the compositions (final volume of 200 μl).

As chemiluminescent agents, Example 19 contained 3'-chloro-4'-hydroxyacetanilide, Example 20 contained 2',5'-dichloro-4'-hydroxyacetanilide, and Example 21 contained 2',3'-dichloro-4'-hydroxyacetanilide.

Table VIII below shows the average light signals generated by the compositions for three replicates in each experiment (10 second integral light units at t=4 minutes) after addition of peroxidase. The "signal to noise" ratio (S/N) is the ratio of the light signal generated by the composition in the presence of horseradish peroxidase to the signal generated from background (no peroxidase).

TABLE VIII

| Composition | Peroxidase Level (pmolar) | Signal | Background Signal | S/N |
|---|---|---|---|---|
| Example 19 | 0 | 0.01 | 0.01 | 1 |
| Example 19 | 0.1 | 0.05 | 0.01 | 5 |
| Example 19 | 1 | 0.54 | 0.01 | 54 |
| Example 19 | 10 | 13.79 | 0.01 | 1379 |
| Example 19 | 100 | 272.37 | 0.01 | $2.72 \times 10^4$ |
| Example 20 | 0 | 0.02 | 0.02 | 1 |
| Example 20 | 0.1 | 0.02 | 0.02 | 1 |
| Example 20 | 1 | 0.03 | 0.02 | 1.5 |
| Example 20 | 10 | 0.07 | 0.02 | 3.5 |
| Example 20 | 100 | 30.46 | 0.02 | 1523 |
| Example 21 | 0 | 0.1 | 0.01 | 1 |
| Example 21 | 0.1 | 0.1 | 0.01 | 1 |
| Example 21 | 1 | 0.1 | 0.01 | 1 |
| Example 21 | 10 | 0.22 | 0.01 | 22 |
| Example 21 | 100 | 5.57 | 0.01 | 557 |

The invention has been described in detail with particular reference to preferred embodiments thereof, but it will be understood that variations and modifications can be effected within the spirit and scope of the invention.

We claim:

1. An aqueous composition for providing a chemiluminescent signal comprising:
   a) an oxidant in an amount of from about 1 to about 10 mmolar,
   b) a low molecular weight cationic surfactant present at from about 0.05 to about 2% above its critical micelle concentration, or a cationic polymer present at from about 0.01 to about 2% by weight,
   c) a buffer to maintain the pH of said composition at from about 6 to about 8.5, and
   d) a substituted acetanilide which is present in a total amount of from about 0.05 to about 10 mmolar as the sole chemiluminescent signal generating reagent which provides a signal in response to the catalytic activity of peroxidase, said substituted acetanilide having the structure (I):

wherein
$R^1$ is hydrogen or alkyl of 1 to 4 carbon atoms,
$R^2$ is hydrogen, alkyl of 1 to 4 carbon atoms, alkoxyalkyl of 1 to 4 carbon atoms, hydroxyalkyl of 1 to 4 carbon atoms, aminoalkyl of 1 to 4 carbon atoms, haloalkyl of 1 to 4 carbon atoms, or alkenyl of 2 to 5 carbon atoms,
$R^3$ is hydrogen or alkyl of 1 to 4 carbon atoms,
at least one of $R^4$ and $R^5$ is an electron withdrawing group having a Hammet sigma value of at least about 0.01, wherein any $R^4$ or $R^5$ which is not said electron withdrawing group is hydrogen, and $R^6$ and $R^7$ are independently hydrogen, halo, cyano or methyl, provided that said composition is substantially free of any other chemiluminescent agent.

2. The composition of claim 1 wherein $R^1$ is hydrogen or methyl, $R^2$ is hydrogen, methyl, methoxymethyl, hydroxymethyl, chloromethyl or ethenyl, $R^3$ is hydrogen or methyl, $R^4$ and $R^5$ are independently hydrogen, halo or cyano, and $R^6$ and $R^7$ are independently hydrogen, chloro or methyl.

3. The composition of claim 2 wherein $R^1$ is hydrogen, $R^2$ is hydrogen or methyl, $R^3$ is hydrogen, at least one of $R^4$ and $R^5$ is chloro or bromo, and $R^6$ and $R^7$ are each hydrogen.

4. The composition of claim 1 further comprising peroxidase or a peroxidase-labeled specific binding molecule.

5. The composition of claim 1 wherein said cationic surfactant is cetyltrimethylammonium bromide or cetyltrimethylammonium chloride.

6. The composition of claim 5 wherein said oxidant is hydrogen peroxide, said buffer is tris(hydroxymethyl) aminomethane, and said substituted acetanilide is 3'-chloro-4'-hydroxyacetanilide or 3'-bromo-4'-hydroxyacetanilide.

7. The composition of claim 1 wherein said oxidant is present in an amount of from about 1 to about 10 mmolar, said low molecular weight cationic surfactant is present in an amount of from about 0.05 to about 2% above the critical micelle concentration, or said cationic polymer is present in an amount of from about 0.01 to about 2 weight %, and said substituted acetanilide is present in an amount of from about 0.05 to about 10 mmolar.

8. A diagnostic test kit for the determination of an analyte catalytically related to peroxidase, said kit comprising, in individual packaging:
   i) the aqueous composition of claim 1, and
   ii) a peroxidase or a peroxidase-labeled specific binding species.

9. The test kit of claim 8 wherein said peroxidase-labeled specific binding species is a peroxidase-labeled antibody or a peroxidase-labeled specific binding ligand analogue.

10. A test device for the detection of peroxidase or an analyte catalytically related to peroxidase, said test device comprising an absorbent carrier material and the composition of claim 1.

11. A method for producing a detectable signal in response to peroxidase comprising:
   A) reacting a peroxidase in the presence of the composition of claim 1 to produce a detectable chemiluminescent signal, and
   B) determining the resulting chemiluminescent signal as a measure of peroxidase.

12. The method of claim 11 wherein said peroxidase is detected as part of a peroxidase-labeled specific binding complex.

13. A specific binding assay for the determination of a specific binding ligand comprising:
   A) forming a peroxidase-labeled specific binding complex of a specific binding ligand with a receptor specific for said ligand,
   B) after separating uncomplexed materials from said peroxidase-labeled specific binding complex, contacting said peroxidase-labeled complex with the composition of claim 1 to produce a detectable chemiluminescent signal, and
   C) determining the resulting chemiluminescent signal as a measure of said specific binding ligand.

14. The method of claim 13 wherein said specific binding ligand is complexed with a first and second receptor therefor, said first receptor being a capture reagent, and said second receptor being a detection reagent which binds with peroxidase or is a peroxidase-labeled reagent, thereby forming a sandwich of said ligand and said first and second receptors.

15. The method of claim 14 for the determination of an antigen as said specific binding species, and wherein said first and second receptors are antibodies specific to said antigen.

16. The method of claim 13 wherein said specific binding ligand competes with a peroxidase-labeled specific binding ligand for a single receptor specific for said specific binding ligand.

17. The method of claim 14 for the determination of a nucleic acid wherein said first and second receptors are oligonucleotides which are complementary to different sequences of said nucleic acid.

* * * * *